(12) United States Patent
Dombrowski

(10) Patent No.: US 12,171,973 B2
(45) Date of Patent: Dec. 24, 2024

(54) DISINFECTING DEVICE FOR LUER ACTIVATED DEVICES

(71) Applicant: Solventum Intellectual Properties Company, Maplewood, MN (US)

(72) Inventor: Alan R. Dombrowski, Woodbury, MN (US)

(73) Assignee: SOLVENTUM INTELLECTUAL PROPERTIES COMPANY, Maplewood, MN (US)

(*) Notice: Subject to any disclaimer, the term of this patent is extended or adjusted under 35 U.S.C. 154(b) by 658 days.

(21) Appl. No.: 17/427,119

(22) PCT Filed: Feb. 19, 2020

(86) PCT No.: PCT/IB2020/051396
§ 371 (c)(1),
(2) Date: Jul. 30, 2021

(87) PCT Pub. No.: WO2020/170169
PCT Pub. Date: Aug. 27, 2020

(65) Prior Publication Data
US 2023/0355948 A1  Nov. 9, 2023
US 2024/0131318 A9  Apr. 25, 2024
US 2024/0226529 A9  Jul. 11, 2024

Related U.S. Application Data

(60) Provisional application No. 62/808,981, filed on Feb. 22, 2019, provisional application No. 62/933,377, filed on Nov. 9, 2019.

(51) Int. Cl.
A61M 39/16    (2006.01)
A61M 39/20    (2006.01)

(52) U.S. Cl.
CPC .......... *A61M 39/162* (2013.01); *A61M 39/20* (2013.01)

(58) Field of Classification Search
CPC ........................... A61M 39/162; A61M 39/20
See application file for complete search history.

(56) References Cited

U.S. PATENT DOCUMENTS

| 8,523,831 B2 | 9/2013 | Solomon |
| 9,750,929 B2 | 9/2017 | Ma |
| 2005/0055008 A1 | 3/2005 | Paradis |
| 2017/0050013 A1 | 2/2017 | Bedoe |
| 2018/0361003 A1 | 12/2018 | Dombrowski |
| 2019/0099593 A1* | 4/2019 | Avula ................. A61M 39/165 |

FOREIGN PATENT DOCUMENTS

WO    2018106508 A1    6/2018

OTHER PUBLICATIONS

International Search report for PCT International Application No. PCT/IB2020/051396 mailed on Jun. 2, 2020, 7 pages.

* cited by examiner

*Primary Examiner* — Bradley J Osinski
(74) *Attorney, Agent, or Firm* — Vorys, Sater, Seymour and Pease LLP

(57) ABSTRACT

A disinfecting device for a Luer-activated device having a septum is disclosed. The disinfecting device includes a cap, a plunger including a standoff and a face, and a disinfectant. When the Luer-activated device is secured to the disinfecting device, the Luer-activated device is engaged with the standoff, but the Luer-activated device septum does not contact the standoff or the face.

15 Claims, 10 Drawing Sheets

DISINFECTING DEVICE FOR LUER ACTIVATED DEVICES

Cross Reference to Related Applications

This application is a national stage filing under 35 U.S.C. 371 of PCT/IB2020/051396, filed Feb. 19, 2020, which claims the benefit of both U.S. Provisional Application No. 62/808,981 filed Feb. 22, 2019 and U.S. Provisional Application No. 62/933,377 filed Nov. 9, 2019, the disclosures of which are incorporated by reference in their entirety herein.

TECHNICAL FIELD

The present disclosure relates to disinfecting devices for Luer-activated devices having a septum, such as needleless connectors.

BACKGROUND

During a hospital stay, many patients may require intravenous and/or arterial line therapy for delivery of treatments such as rehydration fluids, medications, nutrients, blood, and the like. There is often also a need to connect medical tubing to a variety of devices to facilitate the administration of such fluids to a patient. To allow the connection of tubing and components from different manufacturers of a variety of devices with one another, a standard connector type was developed. The connector type generally consists of a male connector or "port" being inserted into a female connector, whereby friction and/or a threading mechanism can keep the connectors together. For infusion or aspiration of fluids to or from an intravenous or arterial access line or device (e.g., a catheter, an intravenous line set, an extension set stopcock, a syringe, a valve) this type of connector is known as a Luer fitting, a Luer connector, a Luer lock, or the like. The dimensions of Luer connectors can be found in ISO Standard 80369-7.

Some female connectors may further include a septum, which may also be referred to as a diaphragm or a displaceable piston. The septum can be moved from a closed position to an open position when a male Luer connector is attached but can spring back to the closed position when the male Luer connector is disconnected. This type of device is commonly called a needleless connector or a Luer-activated valve ("LAV") and devices including a such a Luer connector are referred to herein as Luer-activated devices ("LADs").

While LADs can simplify the administration of fluids by removing needles and reducing open port risks, it is still necessary to disinfect LADs prior to use. This is because outside features of the LAD can be exposed to touch and air contamination, contamination that can lead to undesirable patient outcomes, such as central line-associated bloodstream infections. Disinfection of LADs can be accomplished by a variety of methods, such as, for example, with a disinfecting wipe protocol or conveniently with a disinfecting port protector.

SUMMARY

The disclosed disinfecting device includes cap and a movable plunger in the cap, where the movable plunger contains a liquid, typically a disinfectant, within the cap. The disinfecting device is placed over a Luer-activated device. Actuation of the plunger displaces the liquid to contact the LAD. The plunger has a standoff that provides a surface for the face of the LAD to push against while recessing contact of the disinfecting device from contact with the septum of the LAD. In some instances, the LAD can leak if the plunger presses against the septum. Therefore, the standoff recesses contact with the septum and reduces fluid leakage.

In one aspect, a disinfecting device for a Luer-activated device having a septum, the disinfecting device comprises a cap, a plunger within the cap for retaining disinfectant. The cap comprises an inner wall defining an opening and an interior cavity. The plunger comprises a face, a hole, and a standoff projecting from the face in the direction of the opening. In one embodiment, the standoff is at a perimeter of the plunger. In one embodiment, there are a plurality of standoffs.

The plunger can move from a first position in the interior cavity to a second position in the interior cavity. When the disinfecting device is contacted by a portion of the Luer-activated device, the Luer-activated device engages with the standoffs to move the plunger to the second position In one aspect, a disinfecting device for a Luer-activated device having a septum comprising:
  a cap comprising:
    an inner wall, wherein the inner wall defines an opening and an interior cavity, wherein the interior cavity has an interior cavity first portion proximate the opening and an interior cavity second portion proximate the interior cavity first portion, the interior cavity second portion including an interior cavity base, and wherein the interior cavity first portion is configured to receive and couple with a needleless connector;
  a plunger comprising:
    a face, wherein the face has a perimeter, a diameter, and a hole;
    a standoff extending to a first height in the direction of the opening and generally orthogonal to a plane defined by the face, wherein the standoff is adjacent the face perimeter around the entire face perimeter;
    an inner surface;
    an outer surface; and
    a skirt; and
  a disinfectant;
  wherein the plunger is configured to move from a first position in the interior cavity to a second position in the interior cavity when the standoff is contacted by a portion of the Luer-activated device, wherein the second position is closer to the interior cavity base than the first position, and wherein the Luer-activated device septum does not contact the standoff or the face when the plunger is in the second position.

In one aspect, the disinfecting device for a Luer-activated device having a septum comprises:
  a cap comprising:
    an opening;
    an inner wall defining an interior cavity having an interior cavity base opposite from the opening;
  a plunger within the interior cavity, the plunger comprising:
    a face with a perimeter, wherein the perimeter of the face is adjacent to the inner wall of the cap;
    a collapsible wall;
  a disinfectant in the interior cavity between the cavity base, the face of the plunger and the collapsible wall;
  a vent for fluid passage from the interior cavity to an atmosphere outside the disinfecting device;
  wherein the plunger is movable within the interior cavity from the opening toward the interior cavity base.

Features and advantages of the present disclosure will be further understood upon consideration of the detailed description as well as the appended claims.

Figure 1:
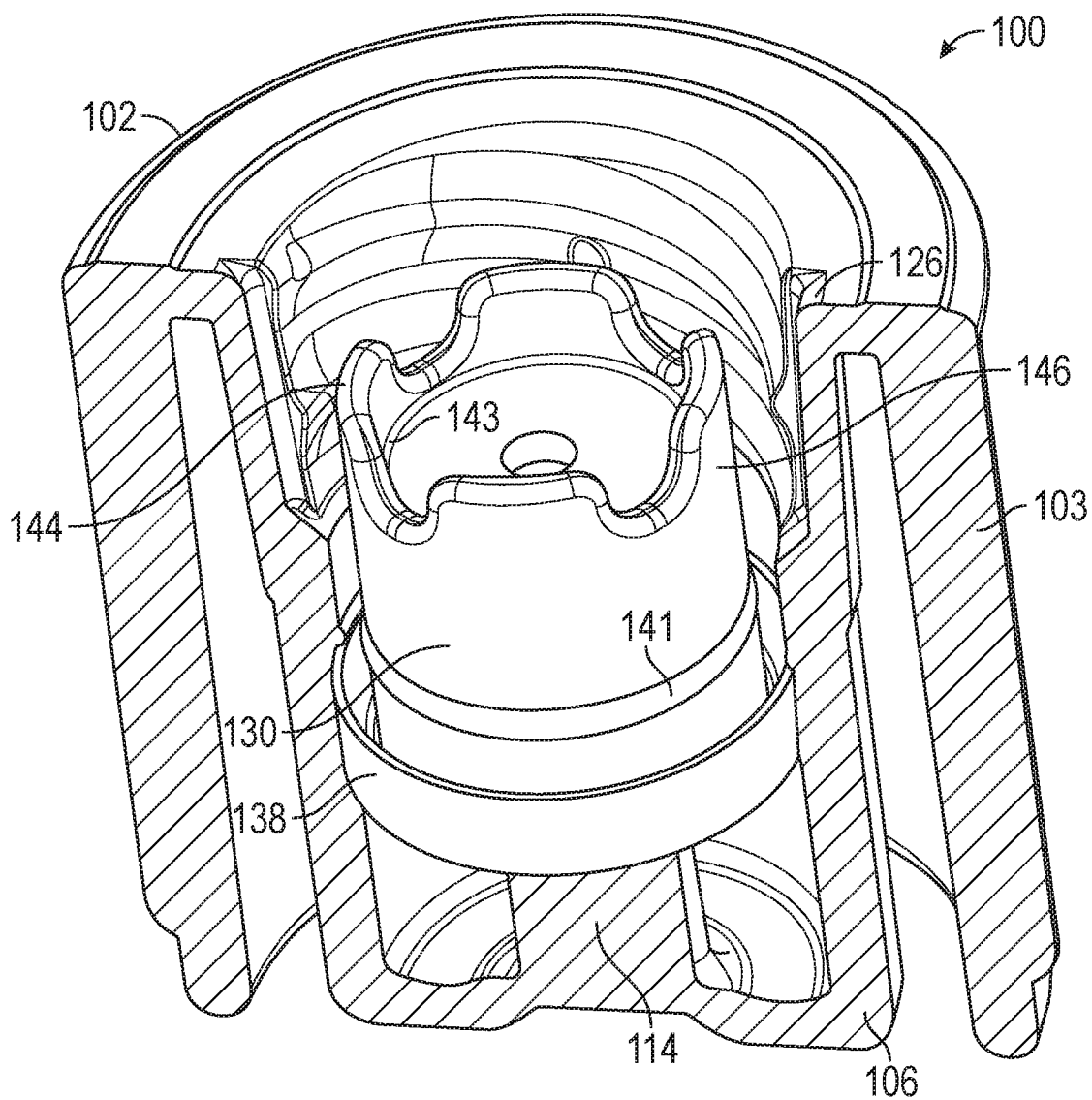
FIG. 1 shows an oblique view of a first embodiment of a disinfecting device of the present disclosure, where the cap is shown as a cross section view and the plunger is shown as a side view, the plunger positioned inside the cap in a pre-activation orientation.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Figure 8:
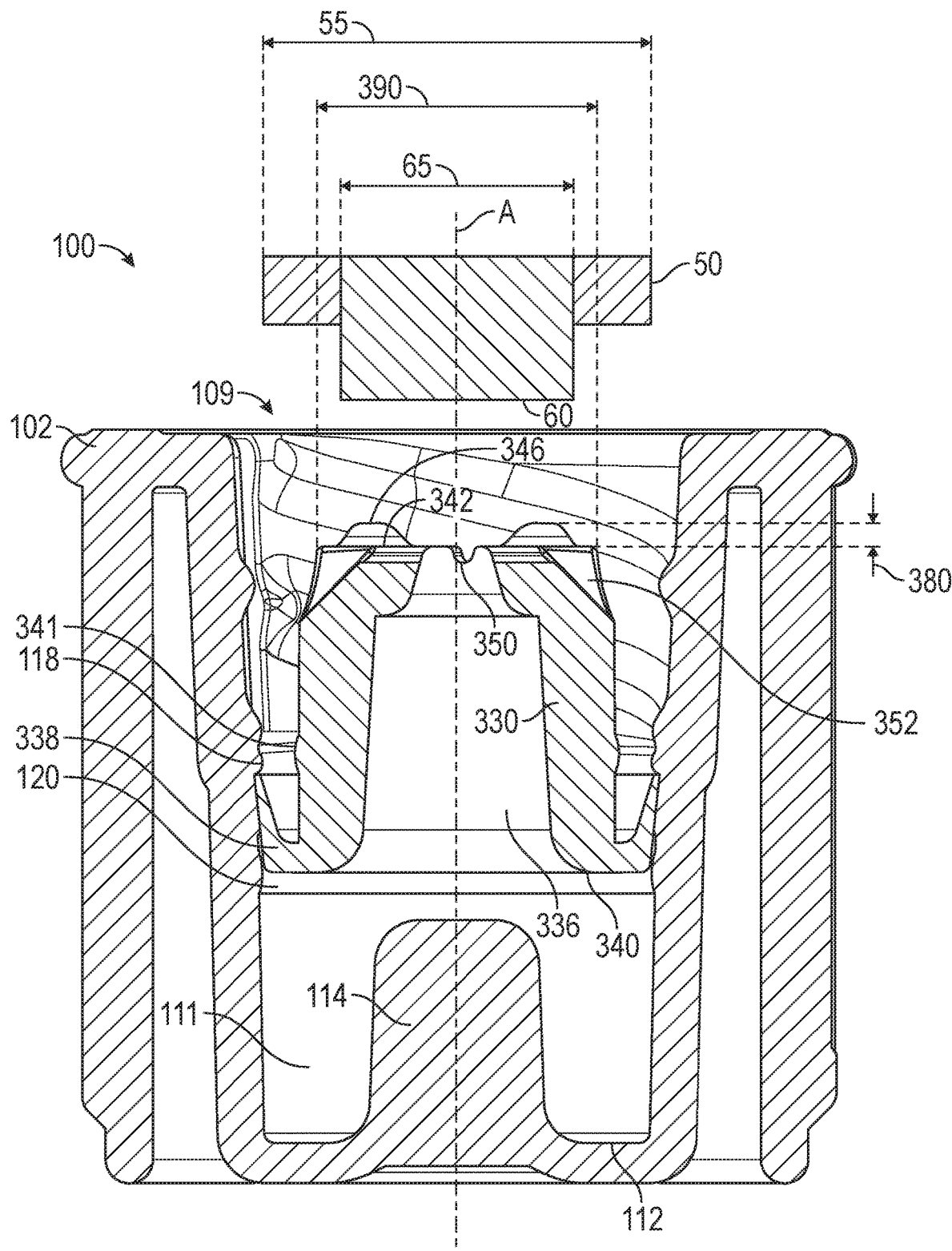
FIG. 8 shows a cross section of a Luer-activated device positioned above the opening of the plunger of FIG. 7 positioned inside the cap in a pre-activation orientation.

Luer-activated devices ("LADs") may be designed so that the septum of the LAD is flush with the face of the LAD when the LAD is in an unpressurized state. Pressure can build up when the LAD is used in an intravenous ("IV") fluid delivery line as part of a pump system or with a hand-held syringe, thus causing the septum of some LADs to protrude from the face of the LAD. This condition is illustrated in FIG. 8, where the septum 60 is shown extending beyond the face of the LAD 50. During use of the LAD, the length of the septum protrusion from the face of the LAD may increase and decrease in response to system pressure, i.e., the length of the septum protrusion may dynamically change. It has been observed that some LADs that dynamically change during use may leak, particularly when septum movement is restricted, for example, when restricted by use of a disinfecting cap.

Some disinfecting caps employ a movable plunger that contains liquid below the plunger before engagement of the cap to the LAD. After the cap is attached to the LAD, the plunger moves, displaces the disinfectant, and the disinfectant wets the face of the LAD. In some cases, the movable plunger of these caps may exert residual force against the protruding septum of the LAD. It has been observed that an LAD experiencing an internal pressure condition may undesirably lead to leaks in the IV system and at the septum/cap interface. Though not wishing to be bound by a particular theory, it is believed that residual force in the disinfecting cap pushing back at the septum can impede travel of the septum and result in such leaks. Thus, minimizing the force the cap and its components exert on the septum during a pressurized condition can reduce or eliminate leaking that can occur at the interface due to the changing length of the septum under pressure conditions.

Despite the presence of disinfecting caps currently in the market space, there is a need for disinfecting devices that can disinfect LADs that may dynamically change length during their use while also reducing leaks that may occur when septum movement is restricted. The disinfecting devices described herein comprise features that address and reduce the fluid leakage that can occur when the disinfecting device engages with an LAD having a septum that protrudes beyond the face of the LAD when the LAD is subjected to internal pressure.

One such disinfecting device employs a plunger standoff that provides a surface for the face of an LAD to push against when the LAD engages with the disinfecting device, which then prevents the LAD septum from contacting either the plunger standoff or the plunger face when the device is connected to the LAD. Thus, the septum is not contacted by the plunger at any time during the application or use of the disinfecting device with the LAD, even when the device is under pressure.

Another such disinfecting device employs a plunger that minimizes the built-up pressure in the device that results when the plunger is moving to the final activation position and eliminates septum contact with the plunger until the septum is at a high enough internal pressure so that the cap cannot activate it. This device also minimizes friction of the plunger as it slides along the cap walls.

Another such disinfecting device employs a plunger retained to the base of the cavity. The plunger further includes a side wall that collapses when a LAD device engages the surface of the standoffs. This device retains disinfecting solution within a cavity defined by the plunger and flexible side walls. The solution is retained within the cavity while the plunger is in a first position, and released through a hole when the plunger compresses and is moved to a second position.

Before any embodiments of the present disclosure are explained in detail, it is to be understood that the phraseology and terminology used herein is for the purpose of description and should not be regarded as limiting. As used herein, the terms "including," "comprising," or "having" and variations thereof encompass the items listed thereafter and equivalents thereof, as well as additional items. All numerical ranges are inclusive of their endpoints and non-integral values between the endpoints unless otherwise stated.

Generally, the disinfecting devices of the present application comprise a cap, a plunger, and a disinfectant contained therein. The disinfecting device is configured to securely fit over an exposed portion of an externally threaded device, such as the Luer threading of an LAD, thus bringing the exposed portion of the LAD in contact with the disinfectant. When the device is attached to an LAD, the plunger slides down the device from a "pre-activation" position to the "final" position. During this movement, a disinfectant solution is forced through an opening in the plunger and acts to disinfect the LAD face. In order for this to happen, before use, the plunger should be maintained in a position such that planes defined by the top and bottom surfaces of the plunger remain parallel to planes defined by the top and bottom surfaces of the cap, as shown, for example, in FIGS. 1 and 2, so that the plunger is properly aligned and at the correct depth in the cap. During use, i.e., activation, of the disinfecting device, the plunger desirably travels straight down into the cap, maintaining the parallel relationships of the planes defined by the plunger and the cap before activation.

The disinfectant can generally be any substance or material that cleans a device (e.g., LAD) of bacterial and/or viral microorganisms and includes antibacterial and antifungal agents, antiseptic or antimicrobial agents, wide-spectrum disinfectants, and/or parasiticides, as well as combinations of such. Exemplary disinfectants include alcohols (e.g., isopropyl alcohol, ethanol), alcohols at various concentrations (e.g., 70%/30% v/v isopropyl alcohol/water), chlorhexidine (e.g., chlorhexidine gluconate, chlorhexidine acetate), povidone-iodine, hydrogen peroxide, soap, hydrochloric acid, chloroxylenol ("PMCX"), polyhexamethylene biguanide ("PHMB"), octenidene, benzalkonium chloride, and combinations thereof. The disinfecting device can remain on the LAD until ready to use, thus protecting the LAD from further contamination.

Figure 2:
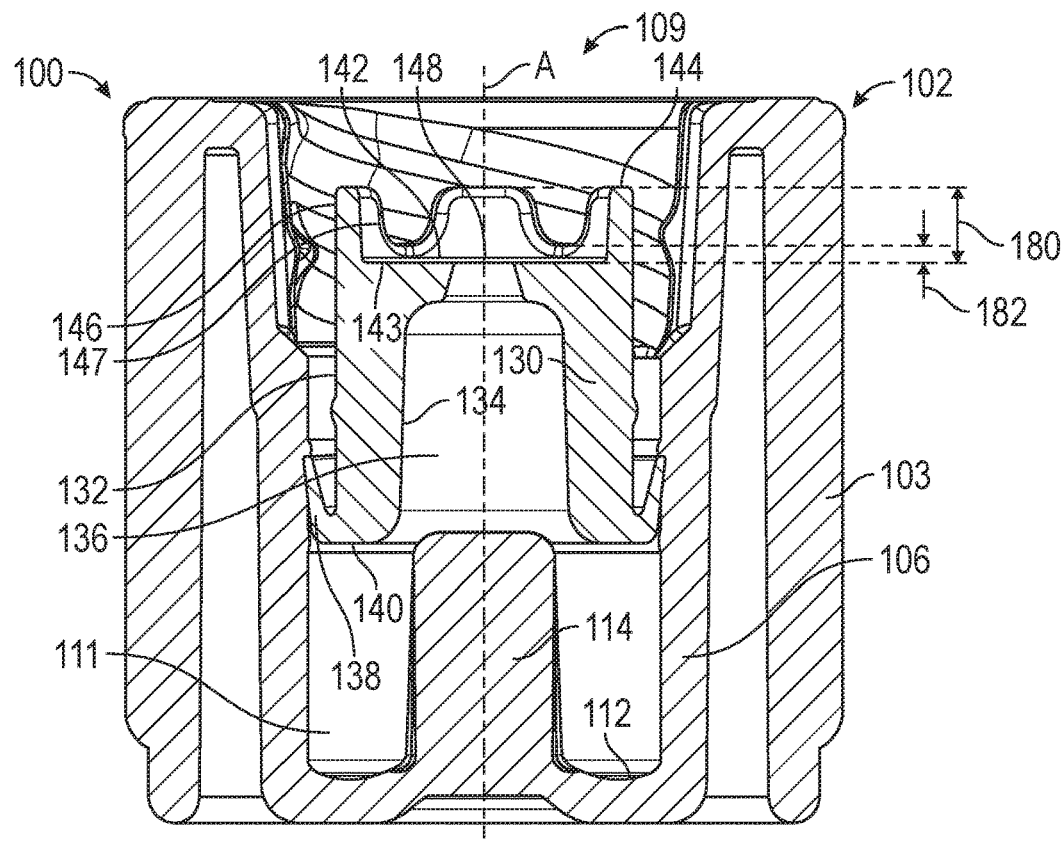
FIG. 2 shows a cross section of the disinfecting device of FIG. 1.
Figure 3:
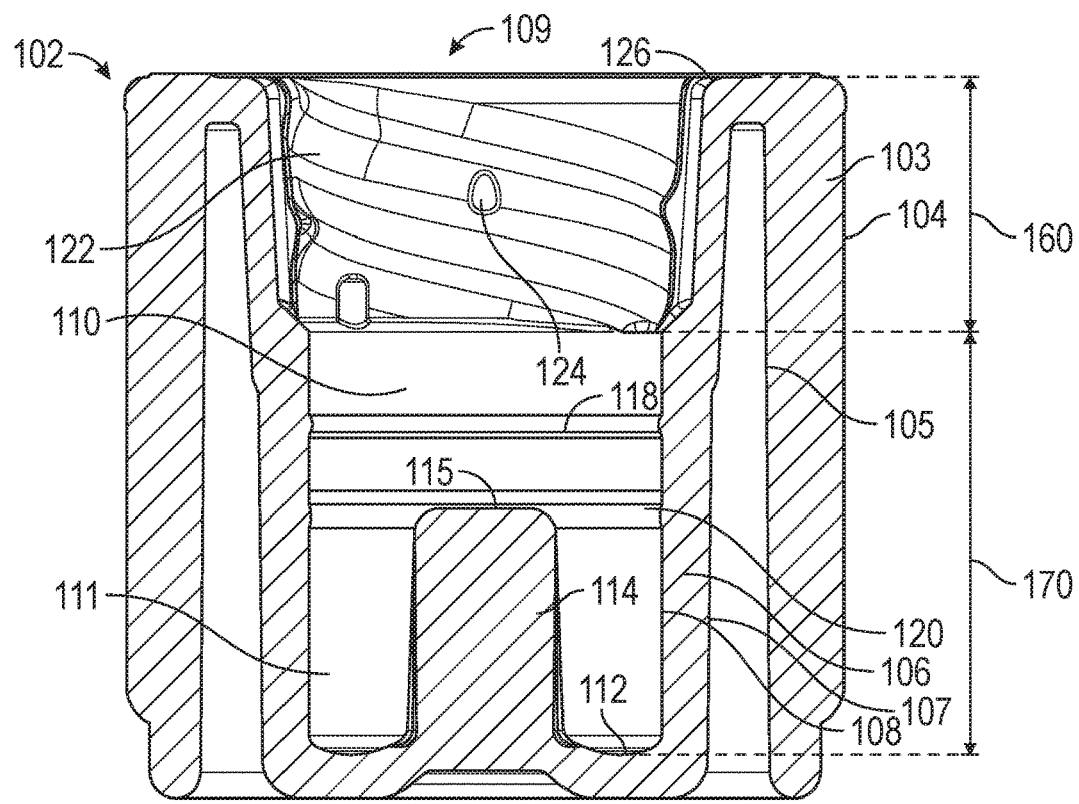
FIG. 3 shows a cross section of the cap of the disinfecting device of FIG. 1.

FIGS. 1 and 2 illustrate a first exemplary disinfecting device 100 of the present disclosure comprising a cap 102 and a plunger 130. Referring to FIG. 3, the cap 102 comprises an inner wall 106 having an opening 109 to an interior cavity 110. The interior cavity 110 includes an interior cavity first portion 160 proximate the opening 109 and an interior cavity second portion 170 proximate interior cavity first portion 160. The cap 102 has an inner wall first surface 107 and an inner wall second surface 108 opposite the inner wall first surface 107. In some embodiments, and as shown in FIG. 3, the cap 102 may include an outer wall 103 joined to the inner wall 106, the outer wall 103 including an outer wall first surface 104 and an outer wall second surface 105 opposite the outer wall first surface 104. The outer wall first surface 104 of the cap 102 optionally includes gripping features (not shown) that are spaced around the outer wall first surface 104 of the cap 102 to facilitate manual manipulation of the cap 102 during use.

A removable protective seal (not shown) can be applied across the opening 109 of the cap 102 to prevent loss of disinfectant in the assembled disinfecting device 100 and maintain sterility of the interior cavity 110 of the cap 102 prior to use. The seal (e.g., a foil seal) can be secured across the opening 109 of the cap 102 by, for example, glue, solvent, or thermal bonding. In some embodiments, the seal may be configured for multiple disinfecting devices 100 such as a strip of foil where individual disinfecting devices 100 can be peeled from the strip as needed. These strips of disinfecting devices 100 can be made conveniently accessible by hanging them, for example, from IV poles or IV sets in patient rooms and on medication carts.

The cap 102 shown in in FIG. 1 has a relatively cylindrical shape, but the cap 102 shape is not particularly limited as long as the coupling mechanism is configured to engage with the LAD. In some embodiments, at least a portion of the cap 102 may have a frustoconical shape. In other embodiments, at least a portion of the cap 102 may have a bulbous configuration (e.g., rounded bottom). The cap 102 may be a unitary structure, as shown in FIG. 1, or made from two or more components joined together. For example, the cap in FIG. 1 could be made by joining a cylindrical-shaped inner wall, a cylindrical-shaped outer wall, and a circular, flat bottom together with glue, welding, solvent, threads, or other attachment mechanism.

The cap 102 can be made from a variety of materials, including plastic, glass, and metal. In some embodiments the cap 102 is made from a thermoplastic material. As used herein, the term "thermoplastic material" means a plastic material that has a softening or melting point and is substantially free of a three-dimensional crosslinked network resulting from the formation of covalent bonds between chemically reactive groups, e.g., active hydrogen groups and free isocyanate groups. Examples of thermoplastic materials include, but are not limited to, thermoplastic polyalkylenes, thermoplastic polyurea, thermoplastic polyimide, thermoplastic polyamide, thermoplastic polyamideimide, thermoplastic polyester, thermoplastic polycarbonate, thermoplastic polysulfone, thermoplastic polyketone, thermoplastic polyethylene, thermoplastic polypropylene, thermoplastic polybutylene terephthalate, thermoplastic polyvinylchloride, thermoplastic acrylonitrile-butadiene-styrene, thermoplastic polyurethane and mixtures of thermoplastic compositions containing one or more thereof. In some embodiments, the cap 102 is made from high-density polyethylene ("HDPE").

As further illustrated in FIG. 3, a coupling mechanism configured to engage with an externally threaded device, such as a LAD, is located on the inner wall second surface 108 in the interior cavity first portion 160 of the cap 102. Coupling mechanisms suitable for use in embodiments of the present disclosure are known in the art and are described, for example, in U.S. patent application Ser. No. 15/623,430 (Dombrowski et al.). The coupling mechanism may be unitary with the cap 102, as illustrated in FIGS. 1-3, or a separate component that is joined to the inner surface of the cap 102 by, for example, glue or welding. The coupling mechanism may be made from the same material as the cap 102, or a different material. In some embodiments, the cap 102 and coupling mechanism are made from HDPE.

The coupling mechanism comprises a thread 122 that originates proximate (i.e., at or near) the opening 109 and spirals downward along the inner wall second surface 108 of the cap 102 to a predetermined depth into the interior cavity first portion 160. The caps 102 of the present disclosure may optionally include a retention feature such as, for example, a lug 124, to minimize or reduce premature disengagement of the coupling mechanism from the LAD. The cap 102 may further include a vent 126, the vent 126 allowing for fluid exchange between the interior cavity 110 and the atmosphere (i.e., pressure release) as the disinfecting device 100 is attached to an LAD.

The length of the interior cavity first portion 160 is sufficient to accommodate a variety of LAD coupling mechanisms, e.g., 0.2 inches (5 mm). It is understood that the length of the interior cavity first portion 160 may vary depending on the particular design of the cap 102. As shown in FIG. 3, the interior cavity second portion 170 is proximate the interior cavity first portion 160 and includes a cavity base 112 and fluid well 111. The interior cavity second portion 170 is typically devoid of thread 122. To prevent IV line leakage and leakage from the septum/cap interface during use that may arise as a result of the plunger 130 contacting the cavity base 112, it has been observed that a ratio of the length of the interior cavity first portion 160 to the interior cavity second portion 170 is desirably greater than 1:1 and less than 1:2. In some embodiments, the ratio of the length of the interior cavity first portion 160 to the interior cavity second portion 170 is in the range of 1:1.1 to 1:1.9, 1:1.2 to 1:1.9, 1:1.3 to 1:1.8, or 1:1.4 to 1:1.7. In some preferred embodiments, the ratio of the length of the interior cavity first portion 160 to the interior cavity second portion 170 is in the range of 1:1.5 to 1:1.7 (e.g., 1:1.6).

The interior cavity second portion 170 may include a first alignment ring 118 and a second alignment ring 120. Referring to FIG. 3, the alignment rings 118,120 are positioned in the interior cavity second portion 170 such that they are located above and below the plunger skirt 138, 338 (described below) and function to help retain the plunger 130 in position, both vertically and concentrically, before activation with an LAD. In some embodiments the alignment rings 118, 120 may be full annular rings that project outward from the inner wall second surface 108 into the interior cavity 110 of the cap 102. In some embodiments, the alignment rings 118, 120 may be annular rings, where each annular ring is subdivided into two or more segments that project outward from the inner wall second surface 108 into the interior cavity 110 of the cap 102. As shown in FIG. 8 the top of the plunger skirt 338 resides below and against the first alignment ring 118 and the skirt base 340 resides above and against the second alignment ring 120 before activation with an LAD. Thus, a two-point method is used to assist in keeping the plunger 130 concentric to the cap 102 and the plunger face 342 flat and at the correct depth with reference to the removable protective seal. The alignment rings 118, 120 keep the plunger 130 positioned concentrically along the longitudinal axis A and prevent the plunger 130 from moving from its pre-activation position when the disinfecting device 100 is subjected to external vibrations, e.g., during shipping.

Figure 4:
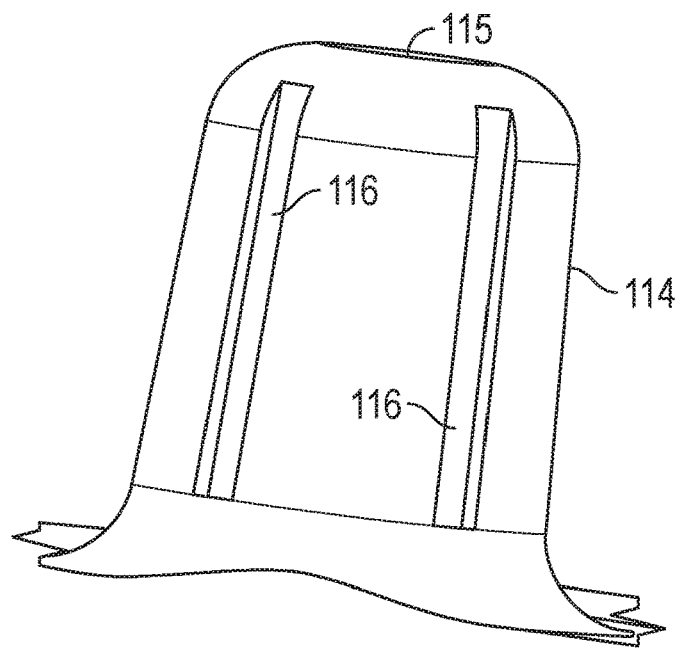
FIG. 4 shows a side view of an embodiment of a center post of the disinfecting device of FIG. 1.

In some embodiments, the cap 102 may include a post 114. Referring to FIG. 3, the post 114 extends in the direction of the opening 109 from the cavity base 112 to a post end 115. In some embodiments, the post 114 may become narrower, i.e., taper, from a thickest dimension, e.g., diameter, at the cavity base 112 to a thinnest dimension at the post end 115. In some embodiments, the post 114 may further include one or more post vents 116, as shown in FIG. 4. While not wishing to be bound to a particular theory, it is believed that the post vents 116 may minimize hydraulic pressure build-up under the plunger 130 while the plunger 130 is sliding downward, i.e., toward the cavity base 112, during activation with an LAD, thereby reducing hydraulic pressure and the resulting back pressure in the IV system which can lead to leakage. In some embodiments the post 114 may be formed as a unitary structure with the cap 102. In some embodiments the post 114 may be formed as a separate component that is joined to the inner surface of the cap 102 by, for example, glue or welding. The post 114 may be made from the same material as the cap 102, or a different material. In some embodiments, the cap 102 and the post 114 are made from HDPE.

Disinfecting devices 100 of the present disclosure further comprise a plunger 130, 230, 330, 430. The plunger 130, 230, 330, 430 is movable within the cap 102 and forms the inner cavity 110 that contains the liquid disinfectant in the disinfecting device 100.

Figure 5:
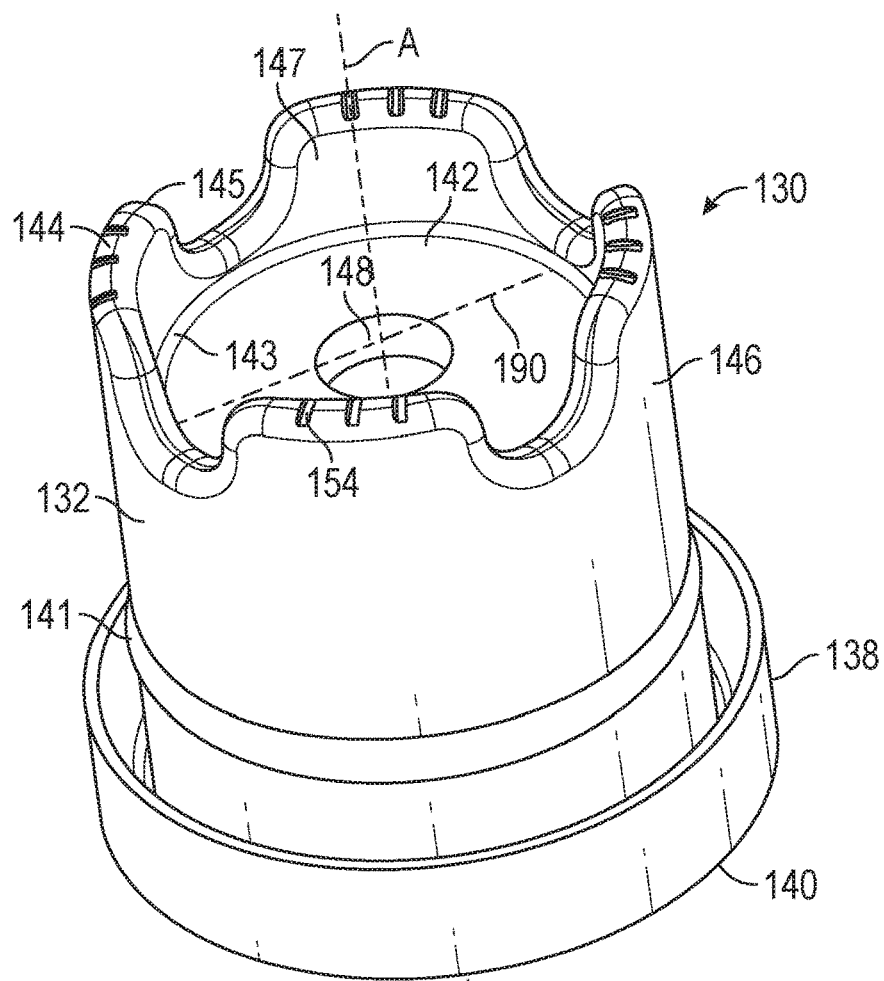
FIG. 5 shows a side view of a first embodiment of a plunger of a disinfecting device of the present disclosure.

A first embodiment of a plunger 130 suitable for use in embodiments of the present disclosure is shown in FIGS. 1, 2, 5, and 10. Referring to FIGS. 2 and 5, the plunger 130 has a relatively cylindrical shape, but the plunger 130 shape is not particularly limited as long as it is configured to nest in the interior cavity 110 of the cap 102. The plunger 130 has outer surface 132 and an inner surface 134 opposite the outer surface 132 and defining a recess 136. The recess 136 is shown having a relatively cylindrical shape but the recess 136 shape is not particularly limited as long as it is configured to accommodate the post 114 of the cap 102 in embodiments where the post 114 is included. For example, in embodiments where the post 114 includes a taper, as described above, the plunger recess 136 would have a complementary taper, thereby guiding the plunger in a path parallel to a longitudinal axis A when the disinfecting device 100 is activated. The plunger 130 has a skirt 138 and a skirt base 140. In some embodiments, the plunger may include a retaining rib 141.

Referring to FIG. 5, the plunger 130 further includes a face 142 normal to longitudinal axis A. The face 142 includes a hole 148, which may be in the center as shown a diameter 190, and a perimeter 143 that abuts a standoff 146 at the base of the standoff inner wall 147 around the entire length of the perimeter 143, i.e., the perimeter is completely encircled by the standoff 146. The hole 148 is shown as a single, circular aperture in the plunger face 142, though different shapes and numbers of apertures for the hole 148 are contemplated. For example, in some embodiments the plunger face 142 can have an oval, square, rectangular, triangular, or irregular shape. In some embodiments, the face 142 may include two or more holes 148.

Referring to FIG. 2, the standoff 146 extends in the direction of the opening 109 and generally parallel to longitudinal axis A from the face 142 to a crest 144 that defines a first height 180. In some embodiments, the standoff 146 has a uniform first height 180 around the entire perimeter of the face 142 (not shown), i.e., the perimeter is completely encircled by the standoff 146 having the uniform first height 180. The first height 180 is selected such that it is sufficient to prevent the protruding septum of an LAD septum from contacting the plunger face 142 during activation, i.e., after the LAD is attached to the disinfecting devices 100.

The standoff 146 is configured to extend far enough from the face 142 to prevent the LAD septum from contacting the face 142 and to be thick enough such that the standoff 146 does not collapse under forces exerted by contact with surfaces of the LAD during activation. In some embodiments, the first height 180 can be 0.054 in to 0.062 in (1.37 mm to 1.57 mm) or preferably 0.056 in to 0.060 in (1.4 mm to 1.5 mm). In some embodiments, the standoff 146 has a first height 180 of 1.47 mm.

In some embodiments the standoff 146 may have thickness, i.e., the distance from the standoff inner wall 147 to the outer surface 132, that is uniform from the crest 144 to the base of the standoff 146, i.e., where the standoff 146 meets the face perimeter 143. In some embodiments, the thickness of the standoff 146 may increase from the crest 144 to the base of the standoff 146, thereby creating additional clearance space for the LAD septum during activation and minimizing surface contact between the LAD septum and the standoff 146, which is desirable to facilitate disinfection, while also providing for a thicker base to better withstand crushing forces exerted by the LAD.

Figure 6:
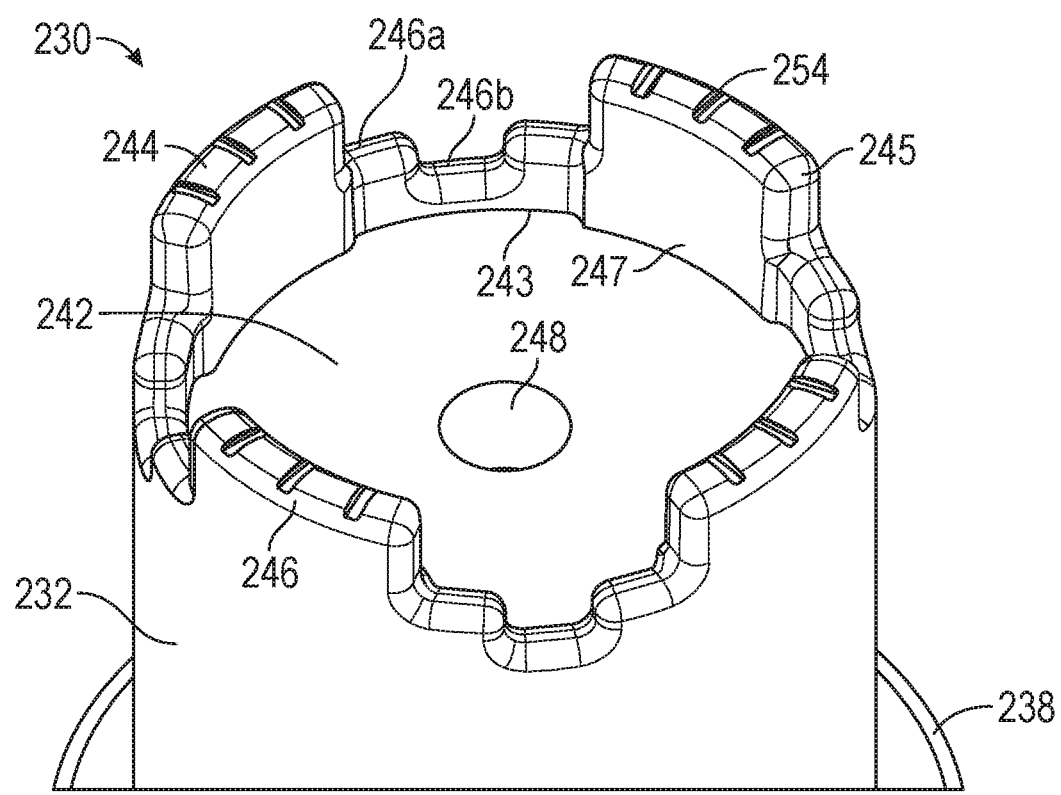
FIG. 6 shows a side view of a portion of second embodiment of a plunger of a disinfecting device of the present disclosure.

In some embodiments, and as shown in FIGS. 5 and 6, the standoff crest 144, 244 may include a channel 154, 254. In embodiments where the standoff 146 has a uniform first height 180 around the entire perimeter 143 of the face 142, the standoff crest 144 desirably includes a plurality of channels 154 so that a path exists for disinfectant to travel as it is forced from the fluid well 111 to the space above the plunger face 142 as the disinfecting device 100 is activated by an LAD. In embodiments where the standoff 146, 246 height varies around the face perimeter 143, 243 it is also desirable for the standoff crest 144, 244 to include channels 154, 254 as it reduces the surface area of the LAD in contact with the standoff 146, 246 and increases the surface area of the LAD in contact with disinfectant. In some embodiments and as shown in FIGS. 5 and 6 the standoff crest 144, 244 may have a radiused profile and contoured edges 145, 245 as it reduces the surface area of the LAD in contact with the standoff crest 144, 244 and increases the surface area of the LAD in contact with disinfectant.

In some embodiments, and as shown in FIG. 2, the standoff 146 has a first height 180 and a second height 182, where the first height 180 is greater than the second height 182 and the transition from the first height 180 to the second height 182 is smoothly graduated, i.e., not stepped. In embodiments of the present disclosure, the standoff 146 has a first height 180 that is at least 50% greater than, 100% greater than, 150% greater than, 200% greater than, 250% greater than, 300% greater than, 350% greater than, or 400% greater than the second height 182. In some preferred embodiments, the standoff 146 has a first height 180 that is 300% to 400% greater than the second height 182. In some embodiments, portions of the standoff 146 at the first height extend for at least 90%, at least 80%, at least 70%, at least 60%, or at least 50% of the length of the standoff crest 144, 244.

In a second embodiment of the plunger 230, shown in FIG. 6, the transition from the first height 180 to the second height 182 may be achieved in a stepwise pattern, e.g., from standoff 246 to standoff 246a to standoff 246b as the standoff 246 encircles the face perimeter 243, providing structural integrity to the standoff 246 while minimizing contact between the standoff 246 and the LAD, thereby increasing the surface area of the LAD in contact with disinfectant. This embodiment of the standoff 146, 246 may also prevent the standoff 246 from being bent during activation.

Figure 10:
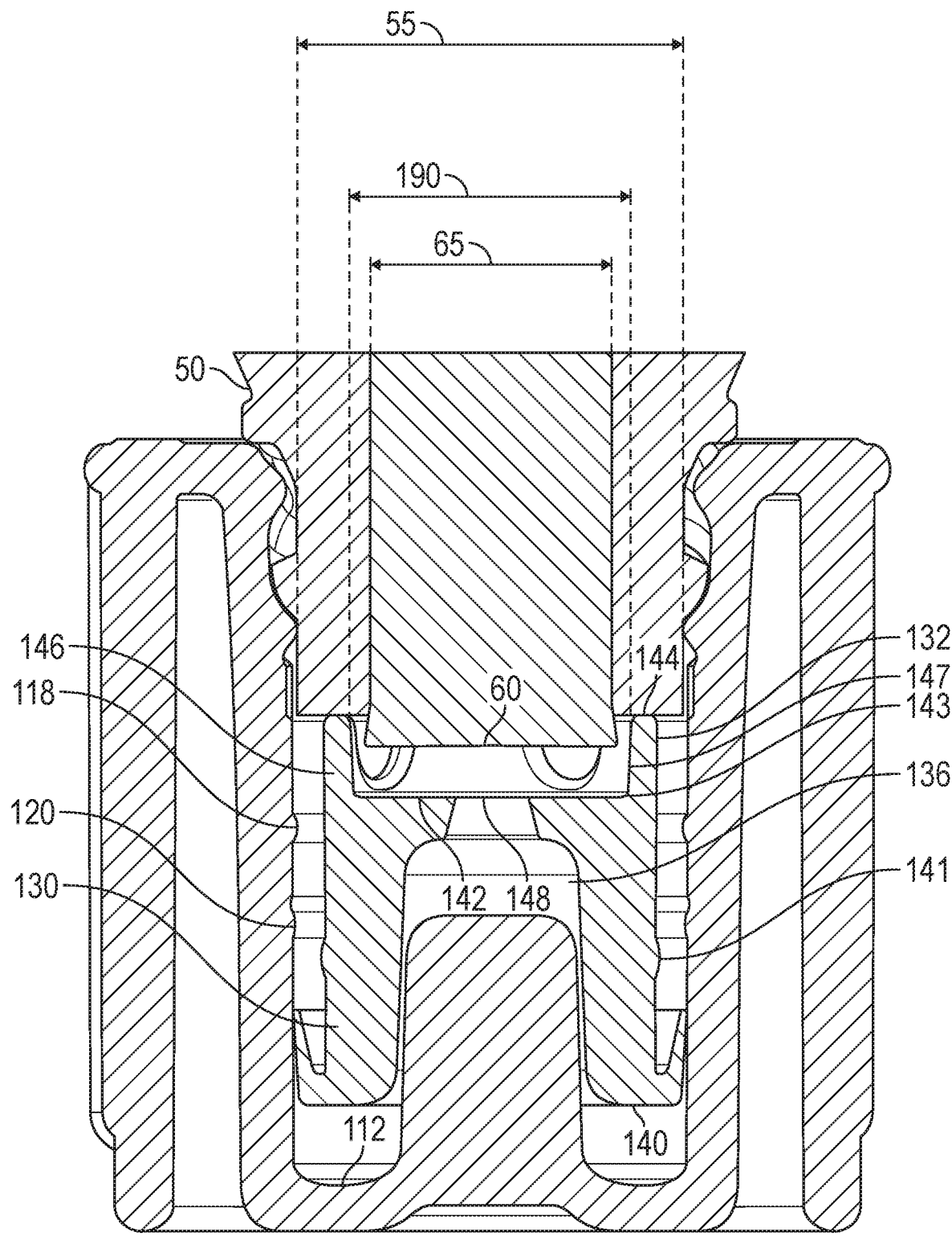
FIG. 10 shows a cross section of the Luer-activated device of FIG. 5 engaged with the plunger positioned inside the cap in a post-activation orientation and the LAD in a pressurized state.

The plunger 130 shown in FIGS. 1, 2, 5, 6, and 10 is configured to move from a first position in the interior cavity 110, as shown in FIG. 2, to a second position in the interior cavity 110 when the standoff 146 is contacted by a portion of the LAD 50 (see FIG. 10). Referring to FIG. 10, the second position is closer to the cavity base 112 than the first position and a portion of the disinfectant (not shown) thereby flows from the fluid welt 111 through the hole 148, thus exposing surfaces of the LAD to the disinfectant. The portion of the LAD 50 that contacts the standoff 146 has a diameter 55 that is greater than the face diameter 190, while the septum 60 has a diameter 65 that is less than the face diameter 190. Thus, upon activation of the disinfecting device 100 with the LAD 50 the septum 60 does not contact either the standoff or the face when the plunger is in the second position. In some embodiments, the face diameter 190 may be at least 1% greater, at least 2% greater, at least 3% greater, at least 4% greater, or at least 5% greater than the septum 60 diameter 65. In some embodiments, the face diameter 190 may be less than 30% greater, less than 20% greater, less than 15% greater, less than 14% greater, or less than 13% greater than the septum 60 diameter 65. In some embodiments, the face diameter 190 may be 1% to 30%, greater, 2% to 20% greater, 3% to 15% greater, 4% to 14% greater, or 5% to 13% greater (e.g., 9% to 11% greater) than the septum 60 diameter 65. In some embodiments, the face diameter 190 may be at least 0.18 in to 0.19 in (4.57 mm-4.83 mm), e.g., 0.186 in (4.72 mm). Desirably in some embodiments, and as shown in FIG. 10, during activation the skirt base 140 may not contact the cavity base 112.

Figure 7:
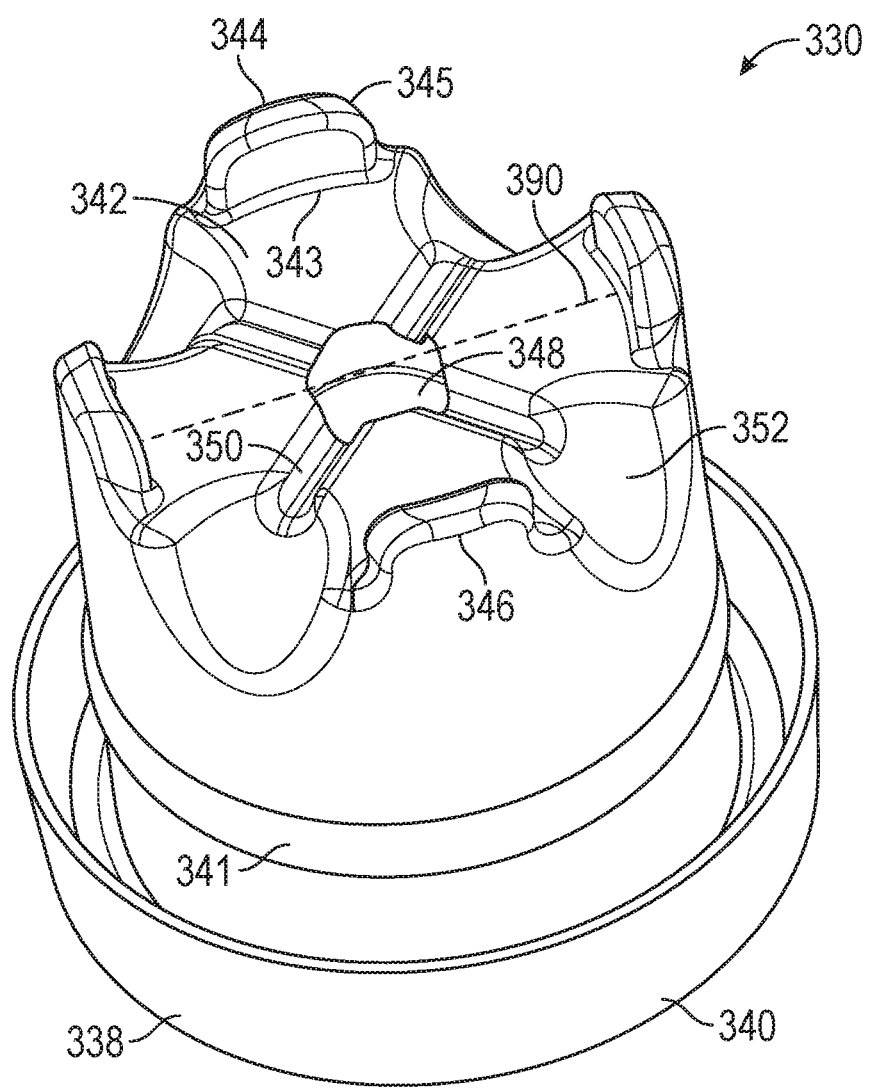
FIG. 7 shows a side view of a third embodiment of a plunger of a disinfecting device of the present disclosure.
Figure 9:
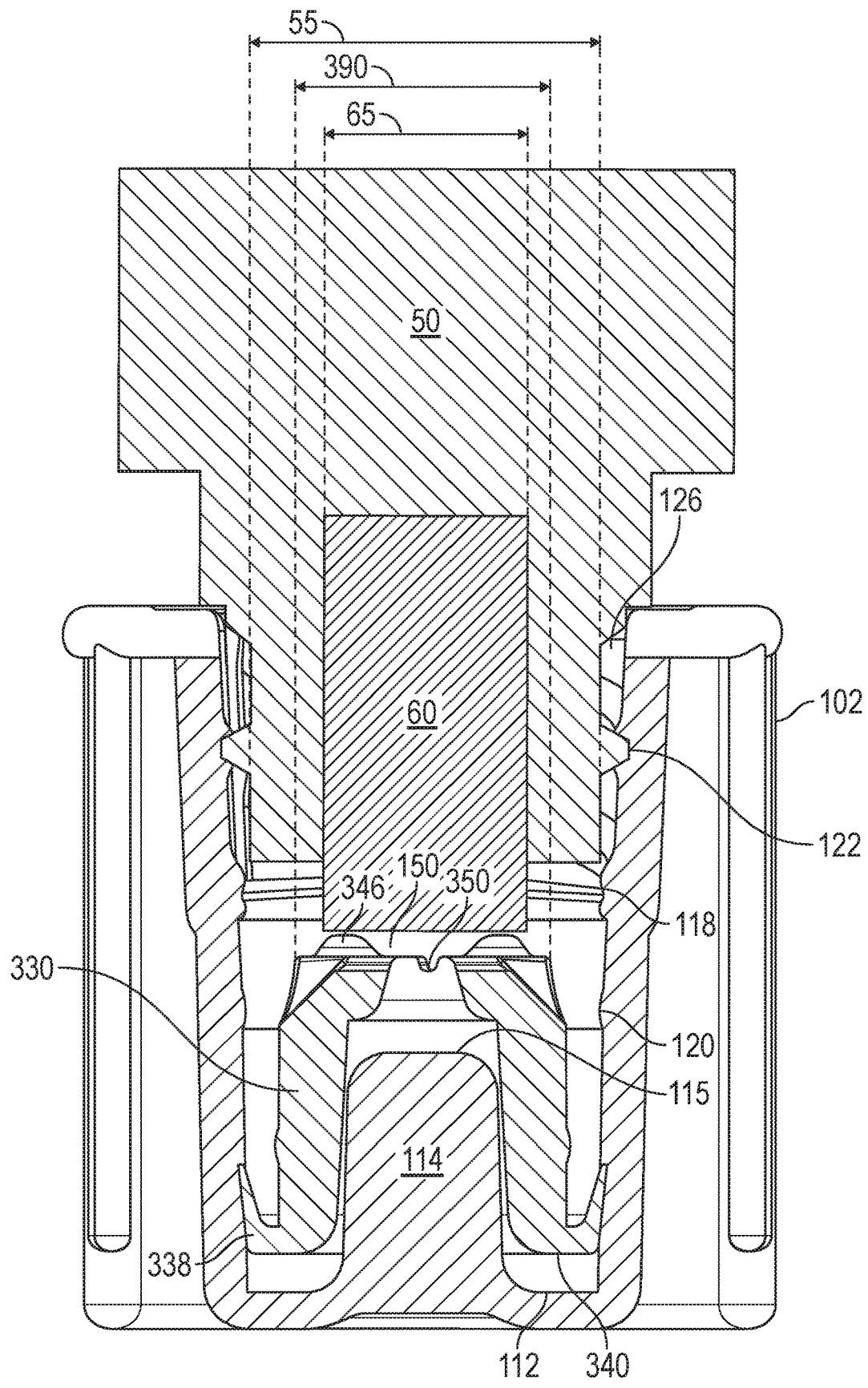
FIG. 9 shows a cross section of the Luer-activated device of FIG. 8 engaged with the plunger positioned inside the cap in a post-activation orientation and the LAD in a pressurized state.

A third embodiment of a plunger 330 suitable for use in embodiments of the present disclosure is shown in FIGS. 7-9. The plunger 330 shares many of the same elements as the plungers 130, 230 shown in FIGS. 1, 2, 5, 6 and 10, differing principally in the face 342 and standoff 346 configurations. Referring to FIG. 7, plunger 330 includes a skirt 338, retaining rib 341, and standoffs 346 positioned around the perimeter 343 of the face 342. Four standoffs 346 are shown in FIG. 7, though three standoffs 346 or more than four standoffs 346, e.g., five standoffs, are contemplated. As with the standoffs described above, the standoff crests 344 may have radiused profiles and contoured edges 345. In some embodiments, standoff crests 344 may further includes a channel (not shown). Generally, the standoffs 346 have a height 380 that is less than that of the standoffs 130, 230, i.e., less than 0.054 in (1.37 mm). Plunger 330 further includes face channels 350 adjacent the hole 348 and extending to the perimeter 343 between the standoffs 346 that allow disinfectant to flow in conditions where the LAD septum 60 is in contact with the face 342 during activation by creating a fluid vent path and thus preventing pressure buildup. In some embodiments, the channels 350 may terminate in a concavity 352 adjacent the perimeter 343.

The plunger 330 shown in FIGS. 7-9 is configured to move from a first position in the interior cavity 110, as shown in FIG. 8, to a second position in the interior cavity 110 when the standoffs 346 are contacted by a portion of the LAD 50 (see FIG. 9). Referring to FIG. 9, the second position is closer to the cavity base 112 than the first position and a portion of the disinfectant (not shown) thereby flows from the fluid well 111 through the hole 348, thus exposing surfaces of the LAD to the disinfectant. As with the plunger embodiments described above, i.e., 130 and 230, upon activation of the disinfecting device 100 with the LAD 50, the septum 60 does not contact the standoff 346 when the plunger is in the second position, i.e., the diameter 390 is greater than the septum diameter 65. Desirably in some embodiments, and as shown in FIG. 9, during activation there is a space 150 between the septum 60 and the plunger face 342 and the skirt base 340 does not contact the cavity base 112. If, however, the septum 60 protrudes further toward the plunger face 342, even contacting the face 342 due to system pressure, disinfectant still has a path to flow through the face channels 350 and concavities 352, thus avoiding pressure build up at any stage of the engagement of the septum 60 with the plunger face 342 and preventing back pressure that can result in leaks. In such circumstances, during activation the gap between the skirt base 340 and the cavity base 112 is greater than 0 mm, thus avoiding pressure build up at any stage of the engagement of the septum 60 with the plunger face 342 and preventing back pressure that can result in leaks.

Figure 11:
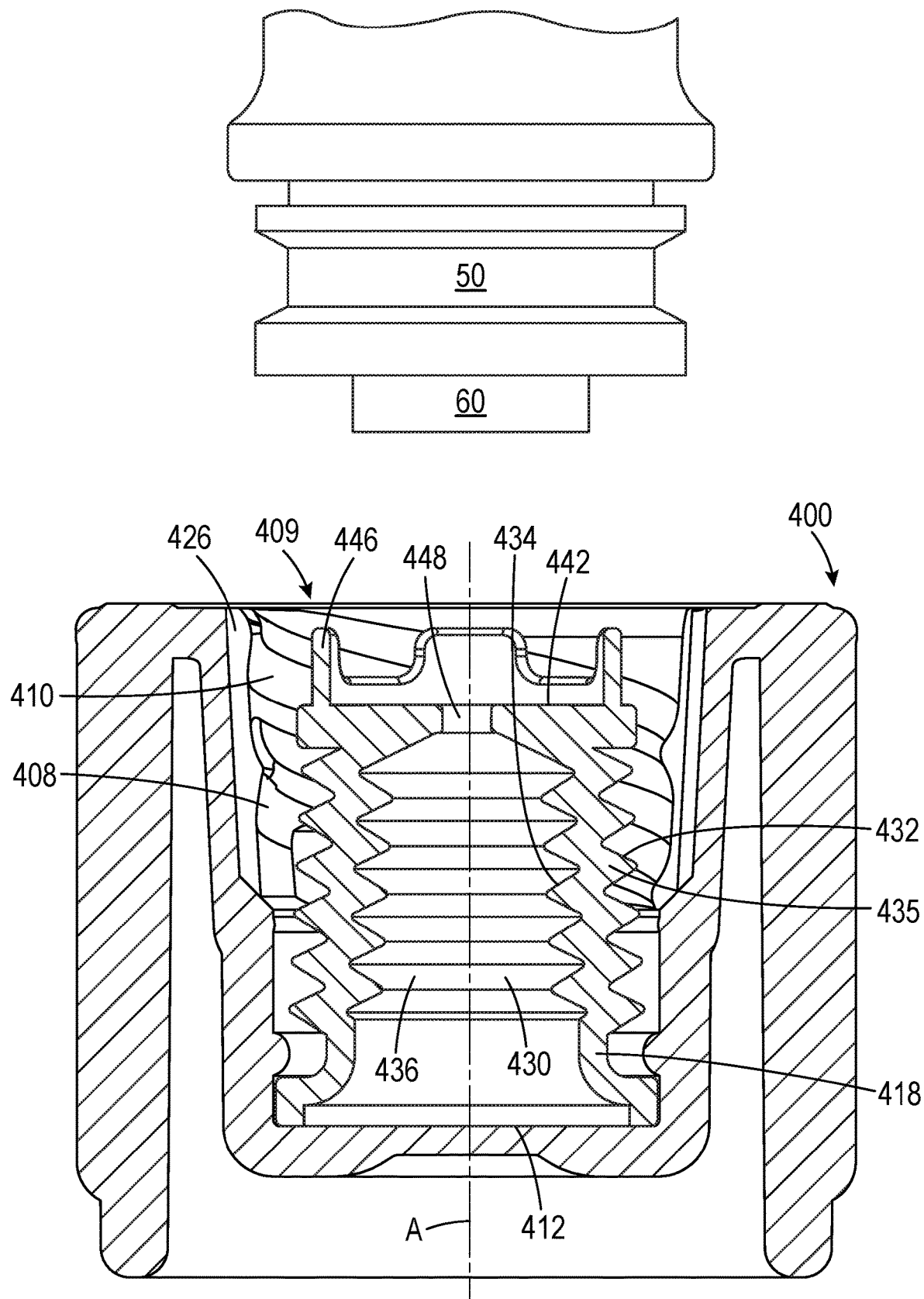
FIG. 11 shows a cross section of the Luer-activated device positioned above the opening of a forth embodiment of a plunger positioned inside of the cap in a pre-activation orientation.
Figure 12:
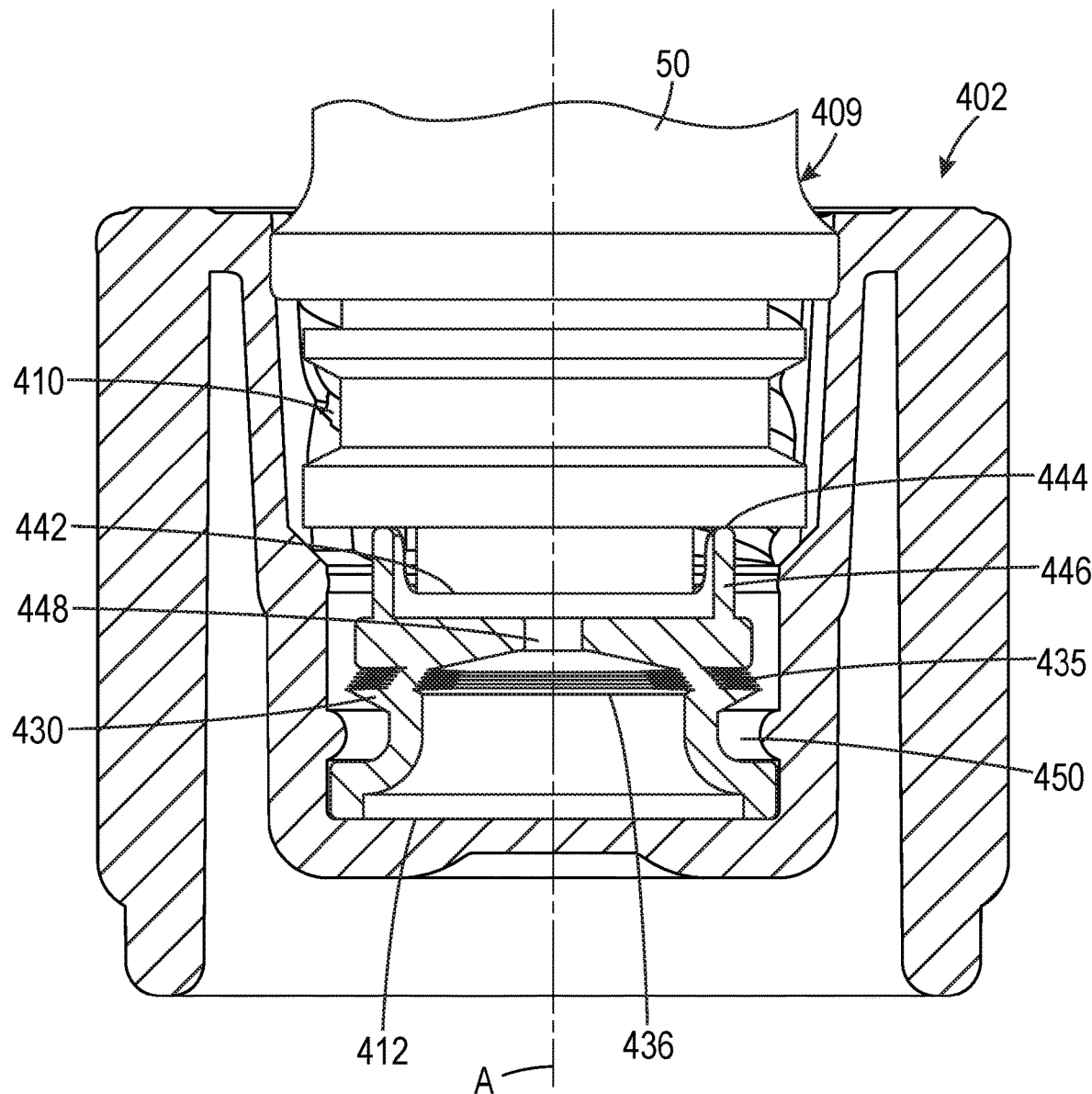
FIG. 12 shows a cross section of the Luer-activated device of FIG. 11 engaged with the plunger positioned inside of the cap in a post-activation orientation and the LAD in a pressurized state.

A fourth embodiment of a plunger 430 in cap 402 suitable for use in embodiments of the present disclosure is shown in FIGS. 11 and 12. As described above, the cap 402 has an opening 409 and cavity base 412 forming an interior cavity 410. The plunger 430 is in the interior cavity 410 of the cap 402. In this embodiment, the plunger 430 includes a plunger face 442 and standoff 446. In this embodiment, the plunger face 442 and standoff 446 includes the features and options as described above for engagement with the LAD 50 and LAD septum 60. The difference in this embodiment, the plunger 430 includes a collapsable wall 435. The collapsable wall 435 has an outer surface 432 opposite a inner surfaces 434. The plunger 430 with the collapsable wall 435 and cavity base 412 define a recess 436 that holds disinfecting fluid within the plunger 430. In this embodiment the recess 436 serves as the fluid well. Hole 448 passes from the recess 436 to the plunger face 442 to allow the liquid within the recess 436 to move out of the recess 436 to the plunger face 442 as described above in other embodiment. To prevent dislodgment of the plunger 430, the plunger 430 is secured within the interior cavity 410. In this embodiment, a first alignment ring 418 friction fits with the outer surface 432 of the collapsable wall 435 to secure the plunger 430 in the interior cavity 410.

In this embodiment, the cavity base 412 functions to define the recess 436. In other embodiment, a separate wall may connected to the collapsable wall 435 to form the recess 436 and be placed adjacent to the cavity base 412. Similarly, in this embodiment, the collapsable wall 435 is placed within the cap 402. In other embodiments, the collapsable wall 435 may for some or all of the cap 402.

FIG. 11 shows the plunger 430 and the recess 436 in a first position with the collapsable wall 435 expanded. FIG. 12 shows the LAD 50 engaging with the disinfecting device 100 with the plunger 430 in a second position. In the second position, the standoff 446 is contacted by a portion of the LAD 50, the plunger 430 is moved closer to the cavity base 412, and the collapsable wall 435 is compressed. The downward movement of the plunger 430 reduces the recess 436 and forces disinfectant out of the recess 436 through the hole 448 and around the LAD 50.

In this embodiment, the collapsable wall 435 functions as a bellows, i.e., similar to an accordion. In other embodiment, the collapsable wall 435 could be any thin, flexible, or collapsable material. For example, the plunger 430 and/or collapsable wall 435 may be made of a soft material such as polyethylene, and blow molded into the shape of a bellows.

Similar to the description above for the other embodiments, the cap 402 may includes one or more inner wall vents 426. The one or more inner wall vents 426 provide a channel for disinfectant to escape the interior cavity 410 and flow along the outside of the LAD 50 when the LAD 50 is threaded onto the cap 402. Thus, the vents prevent pressure from building up within the interior cavity 410 and entering the LAD 50.

As the LAD connects with the disinfecting device, it will be exposed to one or more disinfectants as described above. The disinfectant (not shown) can be a liquid, gel, or foam depending upon the desired configuration. Before activation, i.e., before the disinfecting device is connected to the LAD, the disinfectant resides in the fluid well of the interior cavity below the plunger, which acts to contain the disinfectant in the interior cavity second portion proximate the cavity base. As the disinfecting device is threaded onto the LAD the plunger moves from a first position in the interior cavity to a second position in the interior cavity so that disinfectant flows from the fluid well through the hole, thus exposing surfaces of the LAD to the disinfectant.

Preferably, the plunger 130, 230, 330, 430 is made from a thermoplastic material, as described above for the cap 102. In some embodiments, the cap 102 is formed from a material having a higher flexural modulus than the plunger 130. While not wishing to be bound to a particular theory, it is believed that when the cap 102 is formed from a material having a higher flexural modulus than the plunger 130, 230, 330, 430 upon activation with an LAD, i.e., when the plunger 130, 230, 330 is moved downward toward the cavity base 112, friction between the inner wall second surface 108 of the cap 102 and the plunger skirt 138, 238, 338 is reduced, allowing the plunger 130, 230, 330 to slide more freely, i.e., with reduced opposing force, while the LAD septum is protruding under pressurization and until the plunger 130, 230, 330 reaches its final position. In the fourth embodiment, when the LAD engages the plunger 430 the plunger face 442 and standoffs 446 move downward from a first position to a second position, while the base 412 plunger remains affixed to the cavity base 412. In some embodiments, the cap 102 is made of HDPE and the plunger 130, 230, 330, 430 is made of a blend of HDPE and linear low-density polyethylene ("LLDPE"). In some embodiments, the blend of HDPE and LLDPE forming the plunger 130, 230, 330, 430 comprises at least 15 wt. %, at least 20 wt. %, or at least 25 wt. % LLDPE. In some embodiments, the blend of HDPE and LLDPE forming the plunger 130, 230, 330, 430 comprises less than 45 wt. %, less than 40 wt. %, or less than 35 wt. % LLDPE. In some embodiments, the blend of HDPE and LLDPE forming the plunger 130 comprises 15 wt. % to 45 wt. %, 20 wt. % to 40 wt. %, or 25 wt. % to 35 wt. % (e.g., 30 wt. %) LLDPE.

Disinfecting devices of the present disclosure may be fabricated according to methods known to those of ordinary skill in the relevant arts such as, for example, molding, pressing, casting, additive manufacturing (e.g., three-dimensional printing, generic manufacturing), subtractive manufacturing (e.g., machining, turning, milling, drilling), and combinations thereof. In some embodiments, the cap 102 may be fabricated as one, unitary piece and the plunger 130, 230, 330, 430 may be fabricated as a second, unitary piece. In some embodiments, components of the cap 102, 402 and/or plunger 130, 230, 330, 430 may be fabricated separately and then joined together by a suitable means such as, for example, heating, gluing, soldering, welding, press fitting, cone fitting, snap fitting, sealing, and combinations thereof.

The disinfecting devices of the present application can be used on any LAD. In practice, the user removes the seal that covers the interior cavity of the cap and threads the cap onto the LAD until it is securely engaged. During the engagement process, the face or septum of the LAD is forced against the plunger, causing the plunger to move from a first position to a second position, whereby disinfectant flows from the fluid well through the center hole, thus exposing surfaces of the LAD to the disinfectant The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Thus, the present document discloses, among other things, a disinfecting device and method of making and using such. Various features and advantages of the disinfecting device are set forth in the following claims.

What is claimed is:

1. A disinfecting device for a Luer-activated device having a septum, the disinfecting device comprising:
 a cap comprising:
  an opening;
  an inner wall defining an interior cavity having an interior cavity base opposite from the opening; and a post extending in the direction of the opening from the interior cavity base, wherein the post comprises multiple post vents;

a plunger within the interior cavity, the plunger comprising:
   a face with a perimeter, wherein the perimeter of the face is adjacent to the inner wall of the cap;
   a standoff adjacent the perimeter of the face and extending in the direction of the opening, wherein the standoff comprises multiple crests, and wherein each crest of the multiple crests has a first height configured to prevent the septum of the Luer-activated device from contacting the face of the plunger;
   a hole in the face;
   a recess configured to accommodate the post of the cap; and
   a skirt with a skirt base; and
a disinfectant housed in a fluid well formed between the plunger and the interior cavity;
wherein the plunger is movable within the interior cavity in a direction away from the opening and toward the interior cavity base to push the disinfectant out of the fluid well and through the hole in the face of the plunger.

2. The disinfecting device of claim 1, wherein the face is entirely recessed from the standoff.

3. The disinfecting device of claim 1, wherein in the plunger comprises a collapsible wall.

4. The disinfecting device of claim 3, wherein the fluid well is between the interior cavity base, the face of the plunger and the collapsible wall.

5. The disinfecting device of claim 1, wherein wherein each of the multiple crests is adjacent a trough having a second height that is less than the first height.

6. The disinfecting device of claim 1, wherein the plunger moves from a first position in the interior cavity to a second position in the interior cavity, and wherein, in the second position, the the Luer-activated device contacts the standoff of the plunger, but the septum of the Luer-activated device does not contact the standoff or the face.

7. The disinfecting device of claim 6, wherein the face has a diameter and the septum of the Luer-actived device has a diameter that is smaller than the diameter of the face.

8. A disinfecting device for a Luer-activated device having a septum, the disinfecting device comprising:
   a cap comprising:
      an inner wall, wherein the inner wall defines an opening and an interior cavity, wherein the interior cavity has an interior cavity first portion proximate the opening and an interior cavity second portion proximate the interior cavity first portion, the interior cavity second portion including an interior cavity base, and wherein the interior cavity first portion is configured to receive and couple with a needleless connector; and
      a post extending in the direction of the opening from the interior cavity base, wherein the post comprises multiple post vents;
   a plunger comprising:
      a face, wherein the face has a perimeter, a diameter, and a hole;
      a standoff extending to a first height in the direction of the opening and generally orthogonal to a plane defined by the face, wherein the standoff is adjacent the face perimeter around the entire face perimeter;
      an inner surface;
      an outer surface; and
      a skirt; and
   a disinfectant;
   wherein the plunger is configured to move from a first position in the interior cavity to a second position in the interior cavity when the standoff is contacted by a portion of the Luer-activated device, wherein the second position is closer to the interior cavity base than the first position, and wherein the Luer-activated device septum does not contact the standoff or the face when the plunger is in the second position.

9. A disinfecting device for a Luer-activated device having a septum, the disinfecting device comprising:
   a cap comprising:
      an inner wall, wherein the inner wall defines an opening and an interior cavity, wherein the interior cavity has an interior cavity first portion proximate the opening and an interior cavity second portion proximate the interior cavity first portion, the interior cavity second portion including an interior cavity base, and wherein the interior cavity first portion is configured to receive and couple with a needleless connector; and
      a post extending in the direction of the opening from the interior cavity base, wherein the post comprises multiple post vents;
   a plunger retained to the cavity base by a retention feature, the plunger comprising:
      a face, wherein the face has a center hole;
      a standoff extending to a first height in the direction of the opening;
      a collapsible wall defined by an outer surface and an inner surface; and
      a chamber defined by the collapsible wall; and
   a disinfectant within the chamber;
   wherein the plunger is configured to move from a first position in the interior cavity to a second position in the interior cavity when the standoff is contacted by a portion of the Luer-activated device, wherein in the second position the face is closer to the interior cavity base than the first position.

10. The disinfecting device of claim 9, wherein the cap has a higher flexural modulus than the plunger.

11. The disinfecting device of claim 9, wherein the post extends in the direction of the opening from the interior cavity base to a post end, and wherein the post end does not contact the plunger inner surface when the plunger is in the second position.

12. The disinfecting device of claim 9, comprising a plurality of standoffs.

13. The disinfecting device of claim 9, wherein the standoff height varies around the face perimeter from a first height to a second height, and wherein the first height is greater than the second height.

14. The disinfecting device of claim 9, wherein the standoff comprises a standoff crest and wherein the standoff crest includes a channel.

15. The disinfecting device of claim 9, further comprising a vent for fluid passage from the interior cavity to an atmosphere outside the disinfecting device.

* * * * *